United States Patent [19]

Sackner

[11] Patent Number: 4,648,407

[45] Date of Patent: Mar. 10, 1987

[54] METHOD FOR DETECTING AND DIFFERENTIATING CENTRAL AND OBSTRUCTIVE APNEAS IN NEWBORNS

[75] Inventor: Marvin A. Sackner, Miami Beach, Fla.

[73] Assignee: Respitrace Corporation, Ardsley, N.Y.

[21] Appl. No.: 874,808

[22] Filed: Jun. 13, 1986

Related U.S. Application Data

[63] Continuation of Ser. No. 752,499, Jul. 8, 1985, abandoned, which is a continuation of Ser. No. 553,239, Nov. 18, 1983, abandoned.

[51] Int. Cl.$^4$ ............................................... A61B 5/08
[52] U.S. Cl. ..................................................... 128/721
[58] Field of Search ............... 128/671, 694, 716, 721, 128/722, 723, 725, 774, 785

[56] References Cited

U.S. PATENT DOCUMENTS

| | | | |
|---|---|---|---|
| 3,572,317 | 3/1971 | Wade | 128/723 |
| 3,888,240 | 6/1975 | Reinhold et al. | 128/723 |
| 3,950,799 | 4/1976 | Frank | 128/721 |
| 4,308,872 | 1/1982 | Watson et al. | 128/721 |
| 4,373,534 | 2/1983 | Watson | 128/725 |
| 4,381,788 | 5/1983 | Douglas | 128/722 |
| 4,433,693 | 2/1984 | Hochstein | 128/721 |
| 4,440,177 | 4/1984 | Anderson et al. | 128/725 |
| 4,474,185 | 10/1984 | Diamond | 128/722 |

Primary Examiner—Edward M. Coven
Assistant Examiner—Max F. Hindenburg
Attorney, Agent, or Firm—Stiefel, Gross, Kurland & Pavane

[57] ABSTRACT

The presence and origin of apnea in a newborn subject is detected by separately and concurrently monitoring relative movement of the cranial bones and nasal ventilation. The cranial bones have been found to move with respiration as a function of intrapleural pressure, and monitoring of their movement is accordingly used to generate a signal representative of intrapleural pressure. A nasal cannula, thermistor, thermocouple or $CO_2$ sensors are employed to concurrently generate a signal representative of tidal volume. Absence of changes in both cranial bone movement and respiratory air flow at the nose is indicative of the presence of central apnea, while absence of nasal air flow accompanied by continuing cranial bone movements is indicative of obstructive apnea. The preferred device for detecting cranial bone movement is a surface inductive plethysmographic transducer, although other suitably sensitive motion detecting devices may be employed.

22 Claims, 5 Drawing Figures

METHOD FOR DETECTING AND DIFFERENTIATING CENTRAL AND OBSTRUCTIVE APNEAS IN NEWBORNS

This is a continuation of U.S. application Ser. No. 752,499 filed July 8, 1985, now abandoned, which is a continuation of U.S. application Ser. No. 553,239 filed Nov. 18, 1983, now abandoned.

TECHNICAL FIELD

The present invention generally relates to a method for noninvasively monitoring intrapleural pressure of a newborn subject and, more particularly, to a method for qualitatively and quantitatively measuring the intrapleural pressure of a newborn in a noninvasive manner. The invention additionally relates to a method for noninvasively detecting the presence of, and for differentiating between, central and obstructive apneas and hypopneas in newborn subjects.

BACKGROUND ART

Various techniques and apparatus are known for measuring, and for detecting changes in, intrapleural pressure of a human subject or other living organism. Present techniques are invasive in requiring that at least some portion of a device be inserted into the body as, for example, directly into the pleural or adjacent esophageal space. The most commonly used such device, the esophageal balloon, is based upon the known close correspondence between esophageal and intrapleural pressures. Although the esophageal balloon is perhaps the least objectionable of the available invasive devices with respect to subject discomfort and acceptance, it cannot be used for intrapleural pressure monitoring over extended periods of time and it is particularly difficult to successfully maintain in situ when dealing with newborn subjects. In addition, it has recently been suggested that distortion of the rib cage of preterm and term infants during breathing invalidates the use of esophageal pressure as an estimate of mean pleural pressure.

Maintaining a monitoring probe or device on or about an infant's body is frequently difficult to achieve and applicant is unaware of any prior art techique or device that can be conveniently and noninvasively utilized to continuously monitor intrapleural pressure in a newborn.

Prior art methods and apparatus known for monitoring a newborn to detect the presence of apnea may be designed to sense body movements, as by a detector underlying the subject's mattress during sleep. This method has inherent unreliability since any normal change in body position during sleep can introduce substantial variations into the signal generated by the sensor in response to respiration-related body movements. In addition, such techniques fail to provide a reliable means by which the apnea can be readily differentiated as being either central or obstructive in origin. Immediate differentiation is important in that while central apnea is often treated with drugs, obstructive apnea requires mechanical relief of airway obstruction and, in either event, the appropriate procedure or countermeasure must be introduced at once to restore normal respiration. Even a relatively short delay required to separately diagnose the problem can prove fatal to the newborn. External monitoring devices worn around the rib cage and abdomen, such as magnetimeters, respiratory inductive plethysmographs, and impedance pneumographs may detect central apneas but if respiratory efforts are minimal (i.e. where changes in intrapleural pressure are small) then obstructive apneas may not be diagnosed. Further, if external monitors such as the impedance pneumograph are worn over only the rib cage and abdomen, obstructive apneas will not be diagnosed if respitory efforts are present. Finally, devices sensing air flow at the nose, such as thermocouples, thermistors and $CO_2$ analyzers will detect apneas but fail to differentiate central from the obstructive types.

DISCLOSURE OF THE INVENTION

The present invention is based upon my discovery that the cranial bones of a newborn subject move relative to each other during respiration as a result of a pressure wave transmitted from the pleural space through the cerebrospinal fluid and great veins to the cranial cavity. Detection and monitoring of these movements produces a waveform which closely resembles intrapleural pressure.

According to a preferred form of the invention, a surface inductive plethysmographic transducer—in the form of a length of wire formed in the shape of a loop—is secured on the newborn's head across at least two adjacently-proximate cranial bones to detect relative movement between the bones. Preferably, the transducer is placed over the sagittal suture or the anterior or occipital fontanels. Relative movement of the cranial bones results in proportional movement of the portion of the loop lying thereon, and correspondingly proportional changes in the cross sectional area of the loop. This, in turn, causes a proportional change in the self-inductance of the loop. By incorporating the inductive loop as the inductance element in a variable frequency LC oscillator, changes in loop self-inductance result in proportional changes in the oscillator output signal frequency, which may then be converted to a corresponding voltage signal suitable for display on an output device or further conditioned as desired for the particular application.

It is known that the cranial bones of an infant remain separated until at least nine months of age; thus, the anterior fontanel of the newborn infant may become effectively closed at any time from nine to approximately eighteen months. Consequently, detection and measurement of relative movement between adjacently-proximate cranial bones in accordance with the invention should be possible for at least approximately nine months after birth.

Changes in the output signal of the oscillator are correspondingly indicative of changes in intrapleural pressure of the newborn subject. That signal can be calibrated to provide a measurement of actual intrapleural pressure of the subject by momentarily manually occluding the nose of the subject, measuring the subject's airway pressure while the nose is occluded—as by placing a catheter within the nose just distal to the obstruction or in the mouth—and adjusting the signal to equal the airway pressure measured with the nose occluded. This calibration technique makes use of the known fact that, except during crying, newborns are obligatory nasal breathers. Alternatively, if the baby is intubated with an endotracheal tube because of the need for mechanical respiration assistance, the endotracheal tube can be momentarily occluded and the same calibration procedure carried out.

One particularly significant application of the method of the present invention lies in the detection of apnea in the newborn subject, and in differentiating between central and obstructive apnea. By simultaneously monitoring both cranial bone movement (as indicative of changes in intrapleural pressure) and changes in the velocity of air at the nostrils of the subject's nose (as indicative of inhalation to and exhalation from the lungs), apneas can be detected and differentiated as to type or origin. In the preferred method of the invention, a surface inductive plethysmographic transducer is secured on the newborn's head across at least two adjacently-proximate cranial bones to detect relative movement therebetween and to generate a corresponding signal indicative of changes in intrapleural pressure, and a nasal oxygen cannula is secured at the subject's nose and an output indicative of tidal breathing pressure is generated. By continuously monitoring these two generated signals, central and obstructive apneas can be reliably detected and differentiated. A substantial absence of changes in both the signals is indicative of the presence of central apnea, whereas a substantial absence of changes in the signal generated from the nasal cannula, when accompanied by continuing changes in the output generated from the transducer monitoring movements of the cranial bones, is indicative of the presence of obstructive apnea.

The methods in accordance with the present invention will be more fully apparent from the following detailed description and annexed drawings of the presently preferred embodiments thereof.

BRIEF DESCRIPTION OF THE DRAWINGS

In the drawings, wherein like reference numerals denote similar elements throughout the several views.

BEST MODE FOR CARRYING OUT THE INVENTION

The present invention is based upon my discovery that the cranial bones of a newborn subject move relative to each other during respiration. This movement is a result of a pressure wave transmitted from the pleural space through the cerebrospinal fluid and great veins through the cranial cavity. I have further found that monitoring of these cranial bone movements and generation of a signal corresponding to the bone movements produces a waveform which closely resembles intrapleural pressure. Thus, the relative movements of the cranial bones of a newborn are a function of intrapleural pressure.

The spacing between and relative moveability of adjacently-proximate cranial bones in the newborn exists until at least three months and usually until approximately nine months of age after which the cranial bones gradually become fused to one another. The anterior fontanel, for example, may become effectively closed between nine and eighteen months of age. As a consequence, detection of cranial bone movement during respiration in accordance with the invention will generally be attainable until the newborn is at least nine months old.

The term "adjacently-proximate", as used in the present description and disclosure, is intended to indicate a relationship between adjacently-disposed cranial bones wherein these adjacent bones have confronting or opposed edges. As the cranial bones move with respiration of the newborn subject, their confronting or opposed or "adjacently-proximate" edges correspondingly move relative to each other and, as a consequence, a movement-sensing transducer lying atop and across these opposed edges will detect that movement. Moreover, the confronting edges may be spaced apart by any amount normally present in the cranial bone arrangement of a newborn and, so long as the transducer overlies or is supported by at least two portions of each of the adjacently-proximate bones, their relative movements with respiration will be detectable in accordance with the invention.

Figure 1:
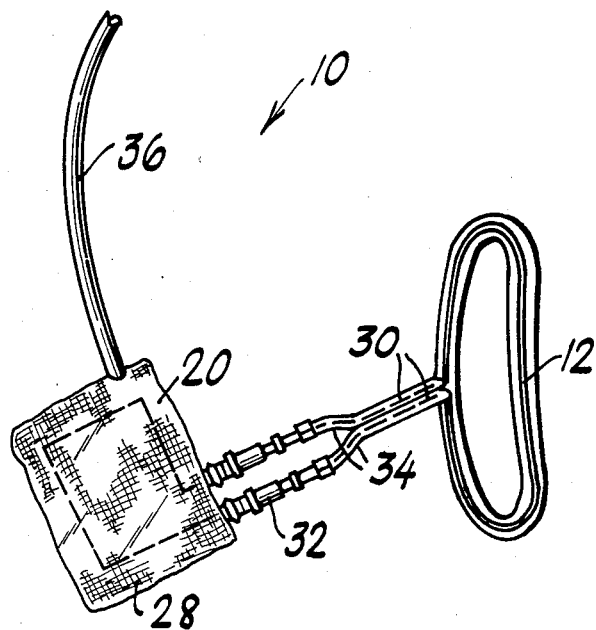
FIG. 1 is a perspective view showing a surface inductive plethysmographic transducer presently preferred for use in monitoring intrapleural pressure in accordance with the method of the invention.

The preferred apparatus utilized to practice the method of the invention is shown in FIG. 1 and there designated by the general reference numeral 10. Transducer 10 is a surface inductive plethysmograph disclosed in my co-pending U.S. application Ser. No. 317,418, filed Nov. 2, 1981, and includes a preferably insulated length of conductive wire 12 formed in the shape of a loop. It is known that the self-inductance of a conductive loop is proportional to the cross sectional area enclosed by the loop. Accordingly, a change in the cross sectional area enclosed by the loop causes a proportional change in the loop inductance.

Figure 3:
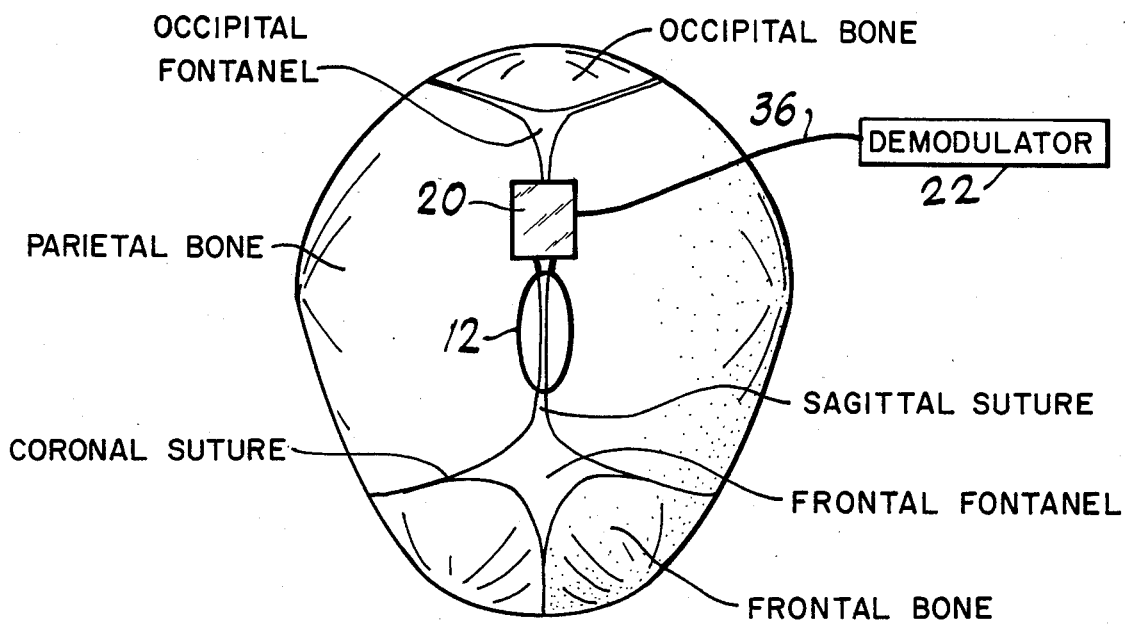
FIG. 3 is a plan view of the skull of a newborn human subject showing the various cranial bones and a preferred placement of the preferred transducer of FIG. 1 on the skull.

In the practice of the invention, relative movement of adjacently-proximate cranial bones is monitored by disposing the conductive loop on the subject such that the loop lies on the surface of the subject's head across at least two of the adjacently-proximate cranial bones. The presently preferred placement of loop 12 over the sagittal suture 14 is shown in the FIG. 3; other preferred locations for the loop include the anterior fontanel 16 and the occipital fontanel 18. Nevertheless, since all of the cranial bones have been found to move relative to each other during respiration, it is within the scope and contemplation of the invention that conductive loop 12 be operatively positioned across at least any two adjacently-proximate cranial bones of the newborn subject. The loop may be secured in place as by taping, or by employing an adhesive preparation such as a collodian solution, although care should be taken not to inhibit movement of the loop upon movement of the cranial bones being monitored.

Relative movement of the cranial bones causes the loop portion lying atop the bones to move. This, in turn, produces a change in the cross sectional area enclosed by the loop and hence in the self-inductance of the loop. By monitoring these self-inductance changes in the manner more fully explained below, an indication of the extent of relative bone movement is provided.

Figure 2:
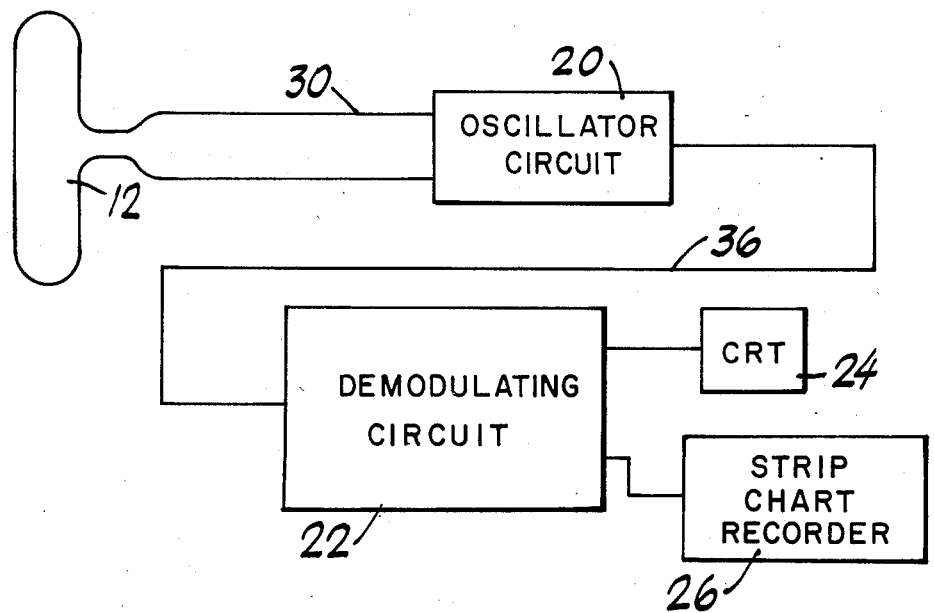
FIG. 2 is a diagrammatic representation of preferred circuitry for measuring the inductance of the comductive loop used in the method of the invention.

Referring now to FIG. 2, a presently preferred circuit for converting the self-inductance of loop 12 to a suitable electrical signal is diagrammatically illustrated. As shown, the circuit includes a variable frequency LC oscillator circuit 20 connected to the ends of conductive loop 12. The resonant frequency of oscillator circuit 20 is determined by an internal capacitor and the inductance of loop 12. This frequency may, for example, be centered about 400,000 Hz, and will vary as the cross sectional area enclosed by the loop varies. Because the relative cranial bone movements being measured are quite small, it is essential that the oscillator circuit have sufficient sensitivity and gain to measure these movements. A suitable oscillator circuit 14 is disclosed in my co-pending U.S. application Ser. No. 317,418, and other appropriate circuits will suggest themselves and be apparent to those skilled in the art once this description is known.

The output signal from oscillator circuit 20 is preferably converted to a suitable voltage signal by a demodulating circuit 22. The output of demodulator 22 is an analog voltage signal having an amplitude which varies in response to changes in the frequency of oscillator 20. An exemplary demodulator circuit 22 is disclosed in my co-pending U.S. application Ser. No. 317,418, and other suitable circuits will be apparent to those skilled in the art once this description is known.

The output signal from demodulator 22 may be displayed on one or more suitable output devices, shown by way of example in FIG. 2 as a CRT terminal 24 and a strip chart recorder 26.

As further seen in FIG. 1, oscillator circuit 20 may be incorporated in a module 28 for securement to the subject's head adjacent conductive loop 12. A pair of insulated wire leads 30 interconnect the oscillator module 28 to loop 12, the leads 30 preferably being joined together in the vicinity of the loop. Connectors 32 in wire leads 30 may be employed to accommodate separation of loop 12 from the oscillator module 28. It will be apparent that the inductance element of oscillator 20 is determined not only by loop 12 but also by leads 30, and that movement of the leads would therefore be disadvantageous as it would affect the oscillation frequency of oscillator 20. Accordingly, leads 30 are preferably substantially rigid, or are secured against movement in some other fashion. The leads 30 in FIG. 1 are rendered rigid by the combination of the substantially rigid wire sheaths 34 and connectors 32. A cable 36 extending from module 26 connects the oscillator circuit 20 to the demodulator 22 and connected output devices 24 and 26.

As the subject exhales and inhales, changes in intrapleural pressure cause corresponding relative movements of the cranial bones. Thus, movements of the cranial bones result in changes in the cross sectional area enclosed by loop 12, and hence in the inductance of the loop, as should be evident. Changes in the loop inductance are monitored by the oscillator circuitry and demodulator circuit 22, and are displayed on the CRT 24 and/or strip chart recorder 26. Consequently, the voltage signal, as so displayed, is an analog waveform indicative of the extent of relative movement of the cranial bones over which loop 12 lies. Changes in the monitored signal have been found to be a linear function of corresponding changes in intrapleural pressure of the subject.

The signal waveform output from demodulator circuit 22 may be calibrated during an initial calibration procedure, whereby subsequent readings will indicate actual intrapleural pressure of the newborn subject. A presently preferred calibration technique makes use of the known fact that newborns are obligatory nasal breathers. In accordance with this procedure, the subject's nose is manually occluded, as by pinching the nose to momentarily close the nasal passages. Since in a closed respiratory system, changes of airway (nasal) pressure equal changes of intrapleural pressure, the subject's airway pressure is then measured by any conventional means while the nose is occluded. The output signal from demodulator circuit 22 is next adjusted to equal the airway pressure measured during the occlusion maneuver, following which the occlusion of the nose is removed to enable the resumption of natural breathing. The output of demodulator circuit 22 will thereafter remain calibrated to intrapleural pressure for natural breathing of the subject.

Although the preferred form of the invention utilizes the disclosed surface inductive plethysmographic transducer 10, it should be recognized and understood that monitoring of the respiration-caused movements of the cranial bones may alternatively be carried out with any transducer sensitive enough to detect the relatively small displacements involved. For example, the cranial bone movements can be monitored by an inductive plethysmographic band or a mercury in silastic strain gauge placed encirclingly about the skull. Other devices, placed over the cranial bones, such as linear displacement transducers, pneumatic pressure transducers and optical transducers, by way of example, can also be employed in accordance with the method of the invention. Use of the disclosed surface inductive plethysmographic transducer 10, however, is particularly advantageous in being relatively small and light weight, and in its consequent ability to be maintained in situ secured on the infant's head during extended periods of time—as during sleep. Furthermore, operative use of transducer 10 in no manner interferes with respiration or with normal body movement of the subject.

The disclosed inventive method for non-invasively monitoring intrapleural pressure in a newborn subject by detection of cranial bone movements finds particular application in the detection and differentiation of central and obstructive apneas. Apneas are considered to be a major cause of sudden infant death syndrome which most often occurs during the first three months of life. The surface inductive plethysmographic transducer 10 is ideally suited as a reliable and easily applied device which may be readily maintained in situ on the infant's head during extended sleep periods to continuously monitor intrapleural pressure changes. In accordance with this particular application of the disclosed invention, the subject's nasal tidal volume is monitored concurrently with the use of an airflow transducer 10 as will hereinafter be understood.

Central apnea is commonly defined as the cessation of neural impulses from the respiratory center of the brain whereby the respiratory muscles fail to contract; in essence, the subject "forgets" how to breath. This condition is accordingly characterized by a lack of fluctuations in intrapleural pressure and, since the respiratory muscles are rendered inoperative so that no inspiration or expiration occurs, tidal volume is essentially zero.

In obstructive apnea, the respiratory muscles are instructed and continue to regularly contract. However, an obstruction of the upper airways (the oro-nasal-pharyngeal region) prevents ventilation of the lungs. Under these circumstances, tidal volume is again zero but, in contrast to central apnea, wide fluctuations in intraesophageal and intrapleural pressure occur as respiratory efforts from muscle contractions continue to take place.

Thus, by monitoring both changes in intrapleural pressure and changes in tidal (breathing) volume, the presence of apneas can be detected and differentiated as to type or origin. Early recognition of the onset of apnea is essential so that an effective treatment or corrective plan can be instituted as rapidly as possible. Since central apnea is most often treated with drugs, whereas obstructive apnea requires physical removal of the obstruction as by an operation or the like, early and immediate differentiation as to the origin of the apnea present is likewise critical.

The inventive technique herein disclosed for identifying the presence and origin of apnea is based at least in part on known observations that the newborn is an obligatory nasal breather, except when crying, and that even during episodes of crying a portion of the breath passes through the nose. Changes in tidal volume are accordingly monitored with a device that noninvasively detects tidal flow at the infant's nostrils. Although any conventionally known device for such purpose can be utilized—such, for example, as a thermistor, a thermocouple or a $CO_2$ sensor (as by mass spectrometry or infrared analyzer techniques)—it is presently preferred that a pediatric nasal oxygen cannula be employed.

Figure 4:
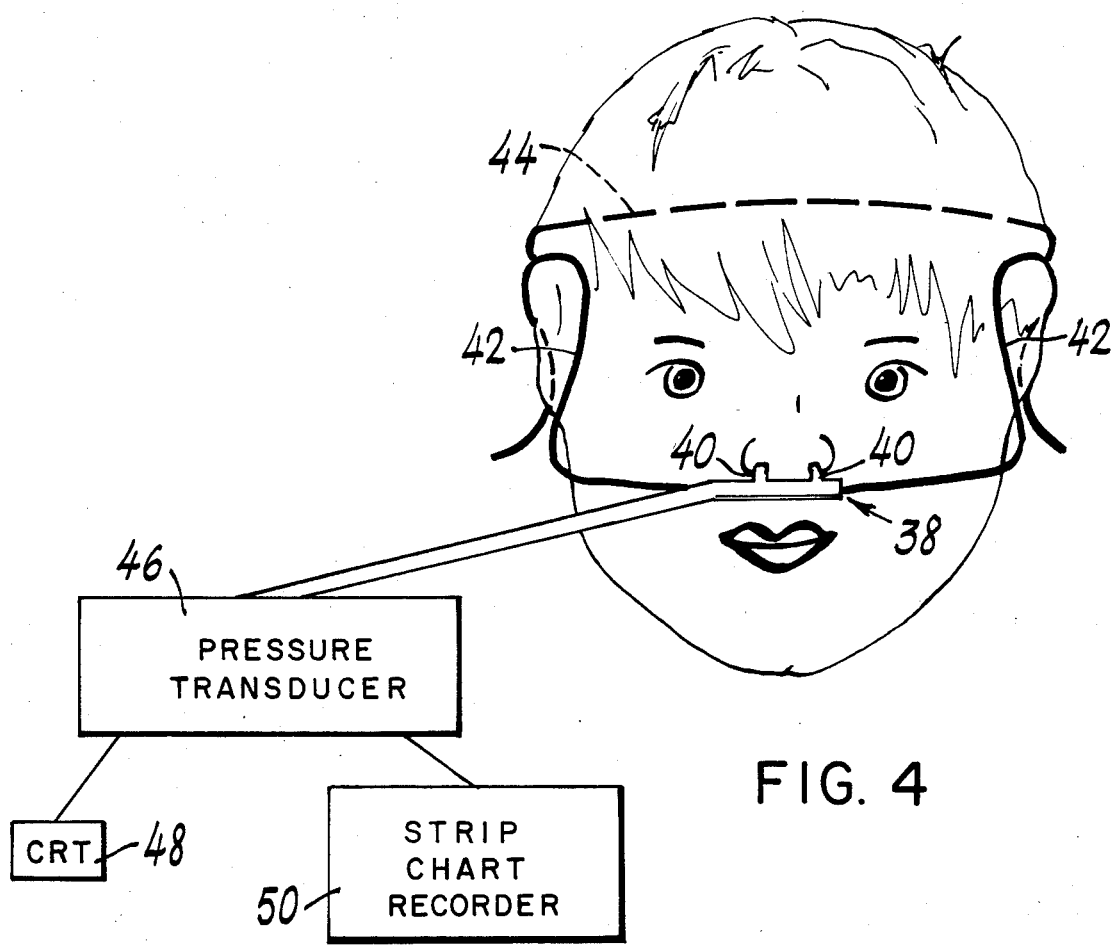
FIG. 4 is a frontal view of a newborn subject showing a nasal cannula in situ in accordance with the inventive method for detecting and differentiating apneas.

Referring now to FIG. 4, a conventional nasal cannula 38 is shown in situ on the newborn subject. Cannula 38 includes a pair of probes 40 which partially project into the subject's respective nostrils. If desired, an alternative cannula configuration (not shown) having but a single nostril projecting probe can be utilized to minimize possible infant discomfort or as the medical condition of the subject might warrant.

Cannula 38 is secured to the patient as, for example, by the use of members 42 that hook about the ears and a cooperating elastic band 44 that encircles the read portion of the head. Alternative methods of securement for mounting cannula 38, as by taping or utilizing an adhesive collodian solution or the like, are also within the contemplation of the invention.

Nasal cannula 38 monitors the infant's breathing by qualitatively measuring pressure changes at the nostrils. A pressure transducer 46 receives the output of cannula 38 and converts the pressure changes to tidal volume changes by integrating the square root of the measured pressures as well known in the art. Transducer 46 may conveniently generate a voltage signal, the amplitude of which varies correspondingly with changes in the pressure detected by this arrangement. Standard output devices such as CRT terminal 48 and strip chart recorder 50 receive the signal output of transducer 46 and display a waveform corresponding to tidal volume.

The inventive method for detecting and differentiating central and obstructive apneas should now be understood. The output of movement transducer 10 (in conjunction with demodulator 22)—which directly indicates relative movement of the cranial bones with respiration—is a varying waveform at least qualitatively representative of the subject's intrapleural pressure. If desired, that output can be calibrated to quantitatively correspond to actual intrapleural pressure, although calibration is not essential in utilizing the apnea detection and differentiation technique herein disclosed.

Concurrent with the monitoring of cranial bone movements by transducer 10, changes in nasal tidal volume are detected utilizing cannula 38 and associated transducer 46. The output signal displayed on the devices 48, 50 is a waveform at least qualitatively representative of changes in the subject's tidal volume with respiration. If desired, the output of cannula 38 can be calibrated by any known method—as, for example, by the technique disclosed by Guyatt et al (American Review of Respiratory Disease 1982, Volume 126, pp. 434-438)—although once again, a quantitative measurement of tidal volume is not essential to effective use of the inventive apnea detection and differentiation method.

By observing the output of each of the monitoring devices—i.e. transducer 10 and cannula 38—during natural or normal respiration, a control or standard value of each of the signals is next obtained. These control values are defined as the average differences between the qualitative trough-to-peak values of each of the waveforms over a period of perhaps ten to twenty respiratory cycles or breaths. Put another way, the control value of the output signal from each detector is the average qualitative change in signal level during normal or natural respiration.

Monitoring of the two output signals or waveforms can be readily interpreted to indicate the onset and origin of apnea present. An absence of changes in the outputs of both cranial bone movement transducer 10 and nasal cannula 38 is indicative of the presence of central apnea. On the other hand, a sudden absence of changes in the output from nasal cannula 38, when accompanied by continuing changes in the signal generated by transducer 10, is indicative of the presence of obstructive apnea. The rapidity with which central and obstructive apnea can be reliably diagnosed in accordance with the disclosed method enables appropriate effective countermeasures to be immediately carried out with corresponding life saving benefits to the newborn subject.

Those skilled in the art will recognize that initial establishment of control values for the output signals generated from transducer 10 and nasal cannula 38 are not essential to the detection of central and obstructive apnea in accordance with the invention. In the former instance, both output waveforms become substantially flat, while in the latter the signal of transducer 10 continues to vary while the output generated from cannula 38 is substantially flat; the control values are unnecessary to each determination. Nonetheless, establishment of control values for the output signals enables intermediate conditions—such as central and obstructive hypopneas—to be diagnosed as well. Central hypopnea is characterized by a proportional diminution or decrease in both intrapleural pressure and tidal volume. Thus, an observation of predetermined partial decreases in the output signals generated from transducer 10 and cannula 38 is suggestive of the presence of central hypopnea. Obstructive hypopnea, or partial upper airway obstruction, might correspondingly be suspected if nasal tidal volume predeterminately decreases from its control value while the amplitude of cranial bone movements persists or increases. Additional advantageous uses for the developed control values during continuous monitoring of intrapleural pressure and tidal volume in accordance with the invention will suggest themselves to those skilled in the relevant art.

Figure 5:
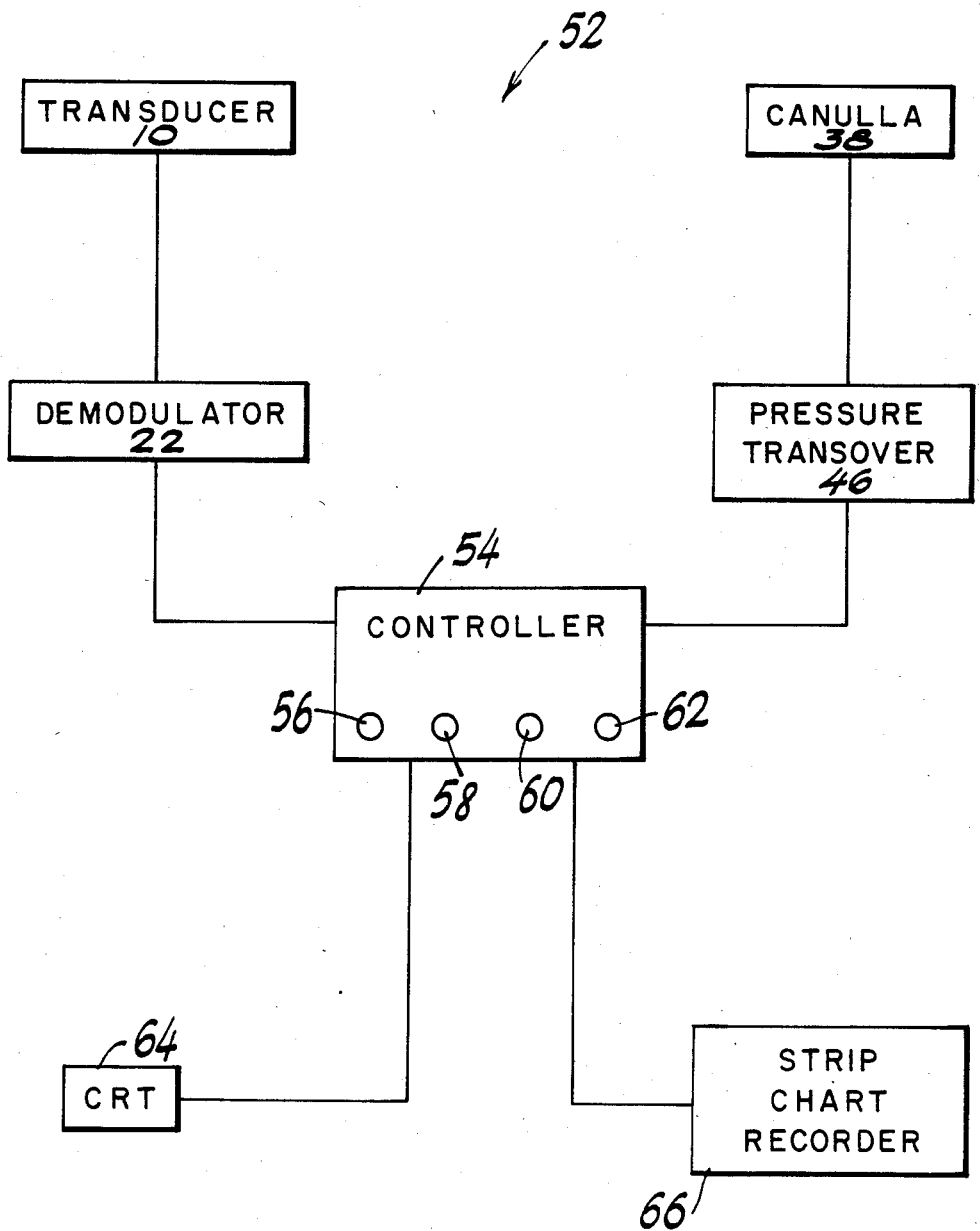
FIG. 5 is a diagrammatic representation of a system for automatically detecting and differentiating apneas and hypopneas in accordance with the invention.

FIG. 5 diagrammatically illustrates an automated system for detecting and differentiating central and obstructive apneas and hypopneas. Automated system 52 incorporates a microprocessor-based controller 54 into which the output signals from each transducer are input. As shown, the output signal generated by the combination of cranial bone movement transducer 10 and demodulator 22, and the output signal generated by the combination of nasal cannula 38 and pressure transducer 46, are interpreted automatically by controller 54 which includes a plurality of alarm indicators 56, 58, 60 and 62. If desired, modulator 22 and/or pressure transducer 46 may be incorporated within controller 54, or they may be externally provided as depicted in FIG. 5. Similarly, additional visual alarm indicators, as well as supplemental auditory alarms, may be incorporated in controller 54. The waveforms input to the controller may also be displayed on suitable output devices such as CRT 64 and/or strip chart recorder 66.

The structural details and construction of controller 54 are deemed to be within the skill of an individual technically competent in the relevant art once this description is known and understood. As such, no specific details are herein disclosed and any suitable controller arrangement for carrying out the apnea detection and differentiation technique of the invention may be employed.

Preferably, controller 54 incorporates a plurality of visual and/or auditory alarms, each corresponding to the diagnosed presence of a particular apnea or hypopnea condition. Thus, by way of example, alarms 56 and 58 may correspond to conditions indicative of central and obstructive apnea, respectively, while indicators 60 and 62 may respectively signal the possible presence of central and obstructive hypopnea. It is also contemplated that controller 54 may include provisions for user-adjustment of the maximum and/or minimum relative signal levels at which each alarm will be activated substantially by the apparatus.

It should also be recognized and understood that although the methods of the present invention have been disclosed and described herein for use with a newborn human subject, they are equally applicable for use with any newborn animal or organism having initial separated cranial bones. Thus, the foregoing description is meant to be by way of example only, and not as a limitation of the scope of the inventive methods and techniques.

There has accordingly been disclosed herein a novel method for measuring intrapleural pressure in newborn subjects, and an application of that method to a novel technique for detecting and differentiating the presence of central and obstructive apneas and hypopneas. While there have been shown and described and pointed out fundamental novel features of the invention as applied to preferred embodiments thereof, it will be understood that various omissions and substitutions and changes in the details of the disclosed methods, and in the form and details and operation of the disclosed devices, may be made by those skilled in the art without departing from the spirit of the invention. It is the intention, therefore, to be limited only as indicated by the scope of the claims appended hereto.

I claim:

1. A method of detecting and differentiating between central and obstructive apneas in a newborn subject, comprising:

mounting an external means for detecting movement across at least two adjacently-proximate cranial bones of the subject to detect relative movement between said bones;

generating a first signal indicative of changes in the relative positions of said cranial bones detected by said means, changes in said first signal being indicative of changes in intrapleural pressure of the subject;

disposing a means for non-invasively detecting variations in tidal breathing at the subject's nostrils;

generating a second signal indicative of variations in tidal breathing detected by said last mentioned means, changes in said second signal being indicative of variations in nasal tidal volume of the subject; and continuously monitoring said first and second signals to detect the presence of and to differentiate between central and obstructive apneas in the subject, whereby a substantial absence of changes in both said first and second signals is indicative of the presence of central apnea, and a substantial absence of changes in said second signal when accompanied by continuing changes in said first signal is indicative of the presence of obstructive apnea.

2. The method according to claim 1, wherein said means mounting step comprises securing a deformable conductive loop across at least said two adjacently-proximate cranial bones of the subject for movement therewith, and said first signal generating step comprises generating a first signal indicative of changes of self-inductance of said loop.

3. The method according to claim 2, wherein said first signal generating step comprises incorporating said loop as the inductance in a variable frequency LC oscillator for converting changes in said self-inductance to corresponding changes in the frequency of the oscillator output signal.

4. The method according to claim 3, further comprising the step of converting changes in the frequency of said LC oscillator output signal to corresponding changes in signal amplitude.

5. The method according to claim 1, further comprising the step of calibrating said first signal to provide a measurement of actual intrapleural pressure of the subject.

6. The method according to claim 3, further comprising the step of calibrating said first signal to provide a measurement of actual intrapleural pressure of the subject.

7. The method according to claim 5, wherein said calibrating step comprises:

momentarily manually occluding the nose of the subject;

measuring the subject's airway pressure while the nose is occluded;

adjusting said first signal to equal said airway pressure measured with the nose occluded; and removing the occlusion of the subject's nose to enable the resumption of natural breathing.

8. The method according to claim 6, wherein said calibrating step comprises:

momentarily manually occluding the nose of the subject;

measuring the subject's airway pressure while the nose is occluded;

adjusting said first signal to equal said airway pressure measured with the nose occluded; and removing the occlusion of the subject's nose to enable the resumption of natural breathing.

9. The method according to claim 5 wherein the newborn subject is intubated with an endotracheal tube, said calibrating step comprising:
- momentarily manually occluding the endotracheal tube;
- measuring the subject's airway pressure while the endotracheal tube is occluded and an inspiratory effort is made;
- adjusting said first signal to equal said airway pressure measured with the endotracheal tube occluded; and
- removing the occlusion of the endotracheal tube to enable the resumption of natural breathing.

10. The method according to claim 6 wherein the newborn subject is intubated with an endotracheal tube, said calibrating step comprising:
- momentarily manually occluding the endotracheal tube;
- measuring the subject's airway pressure while the endotracheal tube is occluded and an inspiratory effort is made;
- adjusting said first signal to equal said airway pressure measured with the endotracheal tube occluded; and
- removing the occlusion of the endotracheal tube to enable the resumption of natural breathing.

11. The method according to claim 1, wherein said means mounting step comprises securing said movement detecting means across the frontal fontanel of the subject to detect relative cranial bone movement.

12. The method according to claim 1, wherein said means mounting step comprises securing said movement detecting means across the occipital fontanel of the subject to detect relative cranial bone movement.

13. The method according to claim 1, wherein said means mounting step comprises securing said movement detecting means across the sagittal suture of the subject to detect relative movement between the parietal bones.

14. The method according to claim 1, wherein said means disposing step comprises securing a nasal cannula on the subject so that a portion of the cannula projects partially into the nostrils, and wherein said second signal generating step comprises connecting said cannula to a pressure transducer to generate an output indicative of tidal breathing pressure.

15. The method according to claim 14, wherein the output of the pressure transducer has a signal amplitude representative of tidal breathing volume.

16. The method according to claim 1, further comprising the step of calibrating said second signal to provide a measurement of actual tidal breathing volume of the subject.

17. The method according to claim 15, further comprising the step of calibrating said second signal to provide a measurement of actual tidal breathing volume of the subject.

18. The method according to claim 16, wherein said calibrating step comprises:
- measuring nasal tidal volume of the subject using an external volume measuring means; and
- adjusting said second signal to equal said nasal tidal volume measured with said volume measurement means.

19. The method according to claim 17, wherein said calibrating step comprises:
- measuring nasal tidal volume of the subject using an external volume measuring means; and
- adjusting said second signal to equal said nasal tidal volume measured with said volume measurement means.

20. The method according to claim 1, further comprising the steps of:
- observing the value of said second signal during natural respiration of the subject to establish a control value of said second signal corresponding to relative tidal volume of the subject during natural respiration; and
- observing the value of said first signal during natural respiration of the subject to establish a control value of said first signal corresponding to relative intrapleural pressure of the subject during natural respiration.

21. The method according to claim 20, said monitoring step comprising continuously comparing said first and second signals to said control values thereof, and generating an alarm when either one or both of said first and second signals decreases by at least a predetermined amount from its respective control value or there exists a substantial absence of changes in one or both of said first and second signals, whereby a substantial absence of changes in both said first and second signals is indicative of the presence of central apnea, a substantial absence of changes in said second signal when accompanied by continuing changes in said first signal, is indicative of the presence of obstructive apnea, a substantial decrease from the control value of both said first and second signals is suggestive of the presence of central hypopnea, and a substantial decrease from the control value of said second signal when unaccompanied by a substantial decrease from the control value of said first signal is suggestive of the presence of obstructive hypopnea.

22. The method according to claim 21, said alarm generating step comprising generating a distinct alarm for each of said enumerated conditions indicative of central apnea, obstructive apnea, central hypopnea and obstructive hypopnea.

* * * * *